United States Patent
Sasaki et al.

(10) Patent No.: US 10,060,890 B2
(45) Date of Patent: Aug. 28, 2018

(54) GAS CHROMATOGRAPH INTERMEDIATE PROCESSING APPARATUS AND GAS CHROMATOGRAPH

(71) Applicant: HORIBA STEC, CO., LTD., Kyoto (JP)

(72) Inventors: Tomohiro Sasaki, Kyoto (JP); Tsuneaki Maeda, Kyoto (JP)

(73) Assignee: HORIBA STEC, CO., LTD., Kyoto (JP)

( * ) Notice: Subject to any disclaimer, the term of this patent is extended or adjusted under 35 U.S.C. 154(b) by 240 days.

(21) Appl. No.: 14/953,703

(22) Filed: Nov. 30, 2015

(65) Prior Publication Data

US 2016/0245783 A1   Aug. 25, 2016

(30) Foreign Application Priority Data

Feb. 20, 2015 (JP) ................ 2015-031661

(51) Int. Cl.
*G01N 30/02* (2006.01)
*G01N 30/84* (2006.01)

(52) U.S. Cl.
CPC ..... *G01N 30/84* (2013.01); *G01N 2030/8435* (2013.01)

(58) Field of Classification Search
CPC .... G01N 30/02; G01N 30/84; G01N 30/8429; G01N 30/8435
See application file for complete search history.

(56) References Cited

FOREIGN PATENT DOCUMENTS

| GB | 2405359 A | * 3/2005 | ............. G01N 30/84 |
| JP | 2013-68501 | 4/2013 | |

* cited by examiner

*Primary Examiner* — Jill A Warden
(74) *Attorney, Agent, or Firm* — Greenblum & Bernstein, P.L.C.

(57) ABSTRACT

To provide a gas chromatograph allowing a substance led out from a measurement target component to reach a reduction reaction part and capable of preventing occurrence of a quantification error while preventing corrosion and sensitivity deterioration of a metal pipeline due to measurement non-related components such as halogen, sulfur and the like. The gas chromatograph includes: an oxidation reaction part into which a sample gas passed through a column is introduced and which oxidizes the measurement target component and converts the resultant measurement target component to a prescribed intermediate component to be led out therefrom; and an intermediate gas flow path for deriving the intermediate component from the oxidation reaction part, and in this configuration, a reagent to be reacted with measurement non-related components is provided in the intermediate gas flow path, and the reagent contains a metal element to be reacted with only oxygen.

9 Claims, 2 Drawing Sheets

GAS CHROMATOGRAPH INTERMEDIATE PROCESSING APPARATUS AND GAS CHROMATOGRAPH

TECHNICAL FIELD

The present invention generally relates to a so-called post-column reaction gas chromatograph and, in particular, to a gas chromatograph intermediate processing apparatus that, causes a sample gas to pass through a column to be separated into each measurement object component which is further subjected to an oxidation-reduction reaction to perform, for example, methane substitution, so that a concentration of each measurement object component contained in the sample gas is measured based on a concentration of the methane.

BACKGROUND ART

Conventionally, using a reaction gas chromatograph of this kind, measurement of concentrations of various kinds of organic compounds contained in, for example, exhaust gas of an internal combustion engine and photochemical smog has been performed. More specifically, as shown in following equations, organic compounds contained in a sample gas are reacted with an oxidizing gas (oxygen) in an oxidation reaction part having an oxidation catalyst and decomposed into $CO_2$ and water. Further, in a reduction reaction part having a reduction catalyst, the $CO_2$ is reduced with reducing gas (hydrogen) to be converted to methane. For example, each of the reactions is as follows:

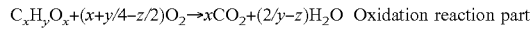
$$C_xH_yO_x + (x+y/4-z/2)O_2 \rightarrow xCO_2 + (2/y-z)H_2O \quad \text{Oxidation reaction part}$$

$$xCO_2 + 4xH_2 \rightarrow xCH_4 + 2xH_2O \quad \text{Reduction reaction part}$$

Then the concentration of the methane generated by the reaction is measured by, for example, FID, and the concentration of the methane is divided by the number of carbon atoms x contained in one molecule of the organic compounds to thereby measure the concentration of the organic compound contained in the sample gas.

Meanwhile, if the sample gas contains, for example, halogen such as chlorine and sulfur, these components are reacted in the reduction reaction part to thereby generate hydrogen halide, sulfuric acid and the like, and this results in causing corrosion of a metal pipeline, deterioration of a reduction catalyst and reduction in sensitivity of the FID.

In order to prevent occurrence of such problems, in the gas chromatograph disclosed in Patent Literature 1, an adsorbent made of a porous material of such as activated carbon is provided in an intermediate gas flow path which connects between the oxidation reaction part and the reduction reaction part, and it is configured so that the measurement non-related components such as halogen and sulfur do not pass through and the measurement non-related components are prevented from reaching the reduction reaction part.

However, the adsorbent such as activated carbon adsorbs not only the measurement non-related components such as halogen and sulfur but also intermediate components $CO_2$ and CO produced by the oxidation reaction part. Therefore, all the components $CO_2$ and CO derived from the measurement target components contained in the sample gas will no reach the reduction reaction part and there occurs a quantitative error in such as a concentration of the measurement target components to be calculated. Similarly, there occurs a quantitative error in the gas chromatograph configured to measure the concentration of $CO_2$ by NDIR without a reduction reaction part.

CITATION LIST

Patent Literature

Patent Literature 1: JP2013-68501A

SUMMARY OF INVENTION

Technical Problem

Therefore, the present invention has been made in order to solve the above problems, and an object thereof is to provide a gas chromatograph intermediate processing apparatus and a gas chromatograph allowing a measurement target component or a substance derived from the measurement target component to reach an analysis part without being impaired and also capable of preventing occurrence of a quantification error while preventing corrosion of a metal pipeline due to measurement non-related components such as halogen, sulfur and the like and preventing deterioration of a catalyst used in a reduction reaction part as well as deterioration in sensitivity of an analyzer.

Solution to Problem

That is, a gas chromatograph intermediate processing apparatus of the present invention includes: an oxidation reaction part into which a sample gas passed through a column is introduced and which oxidizes a measurement target component and converts the resultant measurement target component to a prescribed intermediate component to be led out therefrom; and an intermediate gas flow path into which the intermediate component led out from the oxidation reaction part is introduced. Herein, a reagent to be reacted with measurement non-related components is provided in the intermediate gas flow path or an upstream side of the oxidation reaction part, and the reagent contains a metal element wherein an oxide constituted from only the metal element and oxygen has a decomposition temperature that is equal to or lower than 1,000° C.

With this configuration, the measurement non-related components such as halogen, sulfur and the like passed through the oxidation reaction part react with the reagent to form such as stable compounds to thereby prevent the measurement non-related components from reaching the reduction part and the analysis part. Thus, hydrogen halide, sulfuric acid and the like can be prevented from being produced in the reduction reaction part and it is also possible to prevent a pipeline after the reduction reaction part from being corroded, and prevent the reduction reaction part and the analysis part for measuring the derivative produced by the reduction reaction part and analyzing the measurement target component from being adversely affected. Further, since the reagent reacts with the measurement non-related components to form the stable compounds, it is difficult for the non-related compounds for measurement to peel off from the reagent even after a time lapse, thereby suppressing the measurement non-related components from flowing to the reduction reaction part. In addition, since the oxide of the metal element contained in the reagent is decomposed at a temperature equal to or lower than at 1000° C., it is possible to maintain a state of a pure metal having a high reactivity with the measurement non-related components in a state that the reagent is provided in the intermediate gas flow path or an upstream side of the oxidation reaction part to have a high temperature. Thus, the reaction between the measurement non-related components and the metal element is less likely inhibited by an oxide film.

Moreover, since the reagent reacts with only the measurement non-related components, intermediate components derived from measurement target component such as $CO_2$ or CO produced in the oxidation reaction part can be passed without being reacted or absorbed.

Therefore, the intermediate component is not decreased even in the case where the reagent is provided, it is less likely to occur a quantification error as to a concentration and the like of each measurement target component in the analysis part.

Further, since the color of the reagent is changed by reaction products produced by reaction with the measurement non-related components, it is possible to easily know whether it is a time to exchange the reagent by confirming the color as to whether the reagent can sufficiently react with the measurement non-related components.

As a specific example of the reagent that does not react with or absorb to the intermediate components produced in the oxidation reaction part but reacts only with the measurement non-related components, there can be exemplified a regent that contains a metal element which reacts with halogen compounds or sulfur compounds that is the measurement non-related components.

In order to facilitate a pressure drop due to the reagent to be constant and to make it possibly unnecessary to change a setting of a measurement condition in the gas chromatograph, it is sufficient so long as the reagent is supported by a support and provided in the intermediate gas flow path.

In order to facilitate contacting between the reagent and the measurement non-related components to easily cause the reactions while easily maintaining the pressure loss to be constant, it is sufficient so long as the reagent is supported by a surface of the support to constitute a granule together with the support, and a plurality of granules are filled in the intermediate gas flow path. With this configuration, since it is possible to produce the granules with the granular diameters uniformly formed, also the pressure loss can be easily match a design value.

In order to facilitate molding the reagent, for example, to be homogeneously formed in shape and size of such as granules in a state of being supported by the supports, it is sufficient so long as the supports are made of a synthetic material. With this configuration, the shape and size thereof can be easily controlled as compared with a case of using a natural product as a support, and the pressure loss and the like can be easily made match with a designed value.

In order for a user to easily know a replacement time of the reagent based on a change of a color of the reagent, it is sufficient so long as at least a portion of a pipeline at a portion where the reagent is provided in the intermediate gas flow path is formed to be transparent or translucent.

As a suitable reagent for use in a gas chromatograph that efficiently reacts with the measurement non-related components such as a halogen or sulfur compound to produce a solid substance to easily cause a change in color, there can be exemplified a regent that the metal element contained in the reagent is silver.

As a gas chromatograph intermediate processing apparatus described from another point of view, there can be exemplified such an apparatus that includes: an oxidation reaction part into which a sample gas passed through a column is introduced and which oxidizes the measurement target component and converts the resultant measurement target component to a prescribed intermediate component to be led out therefrom; and an intermediate gas flow path into which the intermediate component led out from the oxidation reaction part is introduced. Herein, a reagent to be reacted with measurement non-related components is provided in the intermediate gas flow path, and wherein the reagent contains silver as a metal element.

As a specific example of the metal element contained in the reagent, there can be exemplified that the oxide of the metal element reacted with only oxygen has a decomposition temperature in a range from 20° C. to 1,000° C.

As a specific example of the gas chromatograph intermediate processing apparatus having a remarkable effect of the present invention, there can be exemplified that further includes a reduction reaction part into which the intermediate component is introduced from the intermediate gas flow path and which reduces the intermediate component and converts the resultant intermediate component to a prescribed derivative to be led out therefrom.

Further, a gas chromatograph according to the present invention includes: the gas chromatograph intermediate processing apparatus; a column through which a sample gas is passed and which separates various measurement target components contained in the sample gas; and an analysis part adapted to measure the intermediate component led out from the oxidation reaction part or the derivative led out from the reduction reaction part to thereby analyze the measurement target components. With this configuration, while solving the problems caused by the measurement non-related components, the substance derived from the measurement target component is allowed to reach the analysis part and the quantitative error can be reduced.

Advantageous Effects of Invention

Thus, according to the gas chromatograph intermediate processing apparatus of the present invention, since the reagent reacting with the measurement non-related components such as halogen and sulfur to form a compound is provided in the intermediate gas flow path into which the intermediate components led out from the oxidation reaction part are introduced, the non-related components and the compounds derived from the measurement non-related components are prevented from reaching the reduction reaction part or the analysis part, thereby allowing the intermediate component derived from the measurement target component produced in the oxidation reaction part to pass through as it is while preventing corrosion of the metal pipeline and deterioration of the reduction reaction part as well as deterioration in sensitivity of the analyzer and also capable of preventing occurrence of a quantification error.

DESCRIPTION OF EMBODIMENTS

The following describes an embodiment of the present invention with reference to the accompanying drawing.

Figure 1:
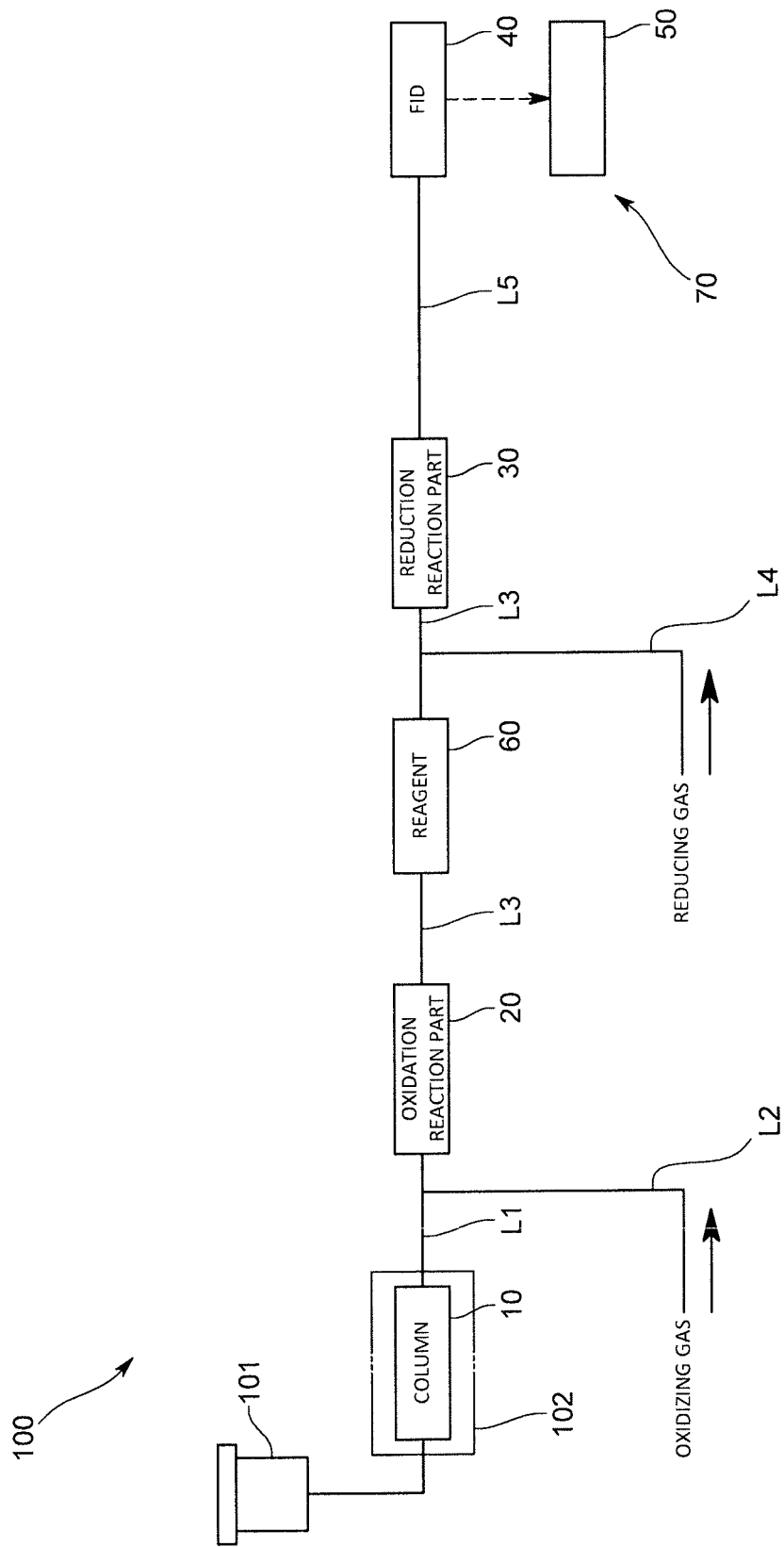
FIG. 1 is a schematic configuration diagram showing an example of a gas chromatograph according to the present embodiment.

A gas chromatograph (also, referred to as "reaction gas chromatograph" hereinafter) 100 according to the present embodiment as shown in FIG. 1 is configured so that a sample gas is passed through a column 10 and separated into each of measurement target components and the measurement target components are converted to a prescribed derivative of a known composition by oxidation reaction and reduction reaction and a concentration of the derivative is detected to thereby measure a concentration of each of the measurement target components contained in the sample gas.

In specific, as shown in FIG. 1, the reaction gas chromatograph 100 of the present embodiment includes: the column 10, an oxidation reaction part 20 that is configured to convert each of the measurement target components contained in the sample gas which has passed through the column 10 to a prescribed intermediate by oxidation; a reduction reaction part 30 that is configured to convert the intermediate to a prescribed derivative by reduction; and an analysis part 70 configured to measure the derivatives contained in the final resultant gas to thereby analyze the measurement target components.

The column 10 is configured to separate the sample gas pumped from pumping means 101 such as a pump into each of the measurement target components to be led out, and it is placed, for example, in a constant temperature bath 102 such as an oven and maintained at a high temperature. In specific, this column 10 is a capillary column with its inner wall coated with a stationary phase, and it is possible to use a suitable known one as the stationary phase.

The oxidation reaction part 20 is configured to be introduced the sample gas which has passed through the column 10 and oxidation gas such as oxygen, oxidizing the measurement target components contained in the sample gas to be converted to prescribed intermediates, thereby producing an intermediate gas containing the intermediates. In specific, as shown in FIG. 1, the oxidation reaction part 20 is configured so that the sample gas is supplied from the column 10 to the oxidation reaction part 20 through a sample gas supply pipeline L1 connecting therebetween and the oxidation gas is supplied through an oxidation gas pipeline L2.

More specifically, this oxidation reaction part 20 includes an oxidation reaction chamber (not shown) having an oxidation catalyst such as palladium inside thereof and first heating means such as a heater (not shown) for heating the oxidation reaction chamber, and it is configured so as to heat the oxidation reaction chamber to a predetermined first set temperature by this first heating means.

This first set temperature is set to 100° C. or higher (for example, 400° C. in the present embodiment) for preventing condensation of moisture generated by the oxidation reaction while promoting the oxidation reaction.

In this oxidation reaction part 20, organic compounds, which are the measurement target components, are oxidized to produce the intermediates such as $CO_2$, CO and $H_2O$, and minute amounts of components such as Cl and S other than the organic compounds contained in the sample gas are oxidized to produce the measurement non-related components such as $Cl_2$ and $SO_2$.

The reduction reaction part 30 is configured so that the intermediate gas led out from the oxidation reaction part 20 and reducing gas such as hydrogen are introduced thereto, and the intermediates produced by the oxidation reaction part 20 are reduced and converted to the prescribed derivatives, thereby producing a final gas containing the derivatives. In specific, this reduction reaction part 30 is configured so that the intermediate gas is supplied thereto via an intermediate gas supply pipeline (i.e., intermediate gas flow path) L3 and the reducing gas is supplied thereto from a reducing gas pipeline L4. In this configuration, a reagent 60 to be reacted with the measurement non-related components such as $Cl_2$ and $SO_2$ is provided in the intermediate gas supply pipeline L3 for supplying the intermediate components led out from the oxidation reaction part 20 to the reduction reaction part 30. The reagent 60 and a configuration related to the reagent 60 will be described in detail later.

Specifically in more detail, the reduction reaction part 30 includes: a reduction reaction chamber (not shown) having a reduction catalyst, for example, nickel, ruthenium, rhodium and the like inside thereof; and second heating means (not shown) such as a heater for heating the reduction reaction chamber, and it is configured so as to heat the reduction reaction chamber (not shown) to a predetermined second set temperature by this second heating means (not shown).

The second predetermined temperature is set to 100° C. or higher (for example, 400° C. equal to the first set temperature in this embodiment) for preventing condensation of moisture contained in the intermediate gas supplied thereto and the final gas to be led out therefrom.

In this reduction reaction part 30, the intermediates such as $CO_2$ and CO contained in the intermediate gas are reduced and a derivative of methane ($CH_4$) is produced. In the conventional gas chromatograph, minute amounts of the measurement non-related components such as $Cl_2$ and $SO_2$ contained in the intermediate gas were reduced to produce such as hydrogen chloride (HCl) and sulfuric acid ($H_2SO_4$). Whereas, in the gas chromatograph 100 of the present embodiment, since the reagent 60 reacts with the measurement non-related components of $Cl_2$ and $SO_2$ to form solid compounds, the components of $Cl_2$ and $SO_2$ are prevented from reaching the reduction reaction part 30 and such as hydrogen chloride and sulfuric acid are not produced.

Further, in the present embodiment, third heating means (not shown) is provided for heating the intermediate gas supply pipeline L3 mentioned above, and it is configured so as to heat the intermediate gas supply pipeline L3 to a predetermined third set temperature by this third heating means.

This third set temperature is set to 100° C. or higher for preventing condensation of the moisture contained in the intermediate gas and it is set to be lower than the first set temperature, for example, 200° C. in this embodiment. That is, the temperature inside the intermediate gas supply pipeline L3 is adjusted so that the oxides of the metal elements contained in the reagent and oxygen are decomposed so that the metal elements can remain as pure metals.

The analysis part 70 is equipped with concentration detecting means 40 that is configured to detect concentration of the methane contained in the final gas and an arithmetic for calculating concentrations of the organic compounds contained in the sample gas based on the concentration of the methane.

The concentrating detecting means 40 is configured so that the final gas is supplied thereto via a final gas supply pipeline (also, referred to as "final gas line" hereinafter) L5 connecting between the reduction reaction part 30 and the concentration detecting means 40, thereby detecting the concentrations of the prescribed derivatives contained in the final gas. In specific, the concentration detecting means 40 of the present embodiment is equipped with a flame ionization detector (FID) allowing the final gas to flow into hydrogen flame of combustion flame and measure ionization current ionized by the hydrogen flame to thereby detect the concentration of the methane contained in the final gas.

The arithmetic device 50 is a general-purpose or dedicated computer which is physically provided with a CPU, a memory, an A/D converter, a D/A converter and the like, and it is intended to function as a concentration calculating part by cooperating the CPU and its peripheral equipment in accordance with a program stored in the memory.

In specific, the concentration calculating part is configured to calculate the concentrations of the measurement target components contained in the sample gas based on the concentrations of the derivatives contained in the final gas obtained by the concentration detecting means 40 as described above. In this concentration calculating part of the present embodiment, the concentrations of the organic compounds contained in the sample gas are measured by dividing the concentration of the methane contained in the final gas by the number of carbon atoms contained in one molecule of the organic compounds of the measurement target components.

Finally, the following describes in detail the reagent 60 provided in the intermediate gas supply pipeline L3.

The reagent 60 of the present embodiment is a metal of silver supported by porous silica formed to be particles as a support. That is, the silver acting as the reagent 60 and the support form a granule. Here, although the silver forms silver oxide as an oxide with oxygen at a room temperature even in some cases, the decomposition reaction of the silver oxide is induced by heating the silver oxide to 1000° C. or lower, and the silver oxide is decomposed into silver and oxygen. Here, since the oxidation reaction part 20 is kept at a temperature of 400° C. as described above, the intermediate gas of a temperature almost near to 400° C. is accordingly allowed to flow into the intermediate gas pipeline L3 in which the reagent 60 is provided. Also, since the intermediate gas supply pipeline L3 per se is heated to a temperature of 200° C. as described above, the reagent 60 is kept at a temperature higher than the decomposition reaction temperature of 200° C. of silver oxide. Therefore, even though the silver of the reagent 60 forms silver oxide, the silver oxide is decomposed and the reagent 60 can remain in a state of pure silver.

The granule is packed and provided at least in a region along an axial direction of the pipe in the intermediate gas supply pipeline L3. Thus, at least the measurement non-related components of $Cl_2$ and $SO_2$ contained in the intermediate gas and the silver of the reagent 60 are reacted to produce the compounds. Thus, the measurement non-related components of $Cl_2$ and $SO_2$ are prevented from directly reaching the reduction reaction part 30 as they are.

That is, the silver of the reagent 60 and $Cl_2$ and $SO_2$ of the measurement non-related components are reacted as follows.

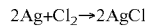

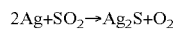

Thus, the $Cl_2$ reacts with the silver to produce brown silver chloride and the $SO_2$ reacts with the silver to produce black silver sulfide. In this way, since the gaseous $Cl_2$ and $SO_2$ react with the silver to be fixed as a solid material, it is possible to prevent the gaseous $Cl_2$ and $SO_2$ from flowing into the reduction reaction part 30. Moreover, since the silver and the measurement non-related components form stable compounds, the measurement non-related components are prevented from being decomposed from the reagent and prevented from flowing into the reduction reaction part 30 even after a time lapse.

Moreover, in order to be able to observe, from the outside, a change in color of the silver chloride or silver sulfide produced by reacting the measurement non-related components with the silver of the reagent 60, at least a portion where the reagent 60 is provided in the intermediate gas supply pipeline L3 is formed to be transparent or translucent. Therefore, it is possible for a user to judge by appearance whether it is the time to replace the reagent 60 by observing a degree of the change in color of the reagent 60.

Meanwhile, the silver of the reagent 60 is less likely to react or absorb with the intermediate components $CO_2$ and CO as compared to the measurement non-related components $Cl_2$ and $SO_2$. For this reason, the intermediate components, i.e., intermediates such as $CO_2$ and CO can pass through the intermediate gas supply pipeline L3 without being trapped by the reagent 60.

According to the reaction gas chromatograph 100 according to the present embodiment configured as described above, since the reagent 60 is provided in the intermediate gas supply pipeline L3 between the oxidation reaction part 20 and the reduction reaction part 30, the measurement non-related components such as $Cl_2$ and $SO_2$ produced by the oxidation reaction part 20 are reacted with the reagent 60 to be removed or reduced as solid compounds, it is possible to prevent hydrochloric acid, sulfuric acid and the like from being produced in the reduction reaction part 30. Therefore, it is possible to prevent adverse effects on the reduction reaction part 30, the pipeline and the concentration detecting means 40.

Moreover, since this reagent 60 is silver but not an adsorbent, it is hardly reacted or absorbed with the intermediate gas components such as $CO_2$ and CO derived from the measurement target components led out from the oxidation reaction part 20 as compared to the measurement non-related components such as $Cl_2$ and $SO_2$. Therefore, substantially all of the intermediate components are allowed to reach the reduction reaction part 30 and the concentration of the methane contained in the final gas corresponds to the concentration of the actual measurement target components to thereby secure the measurement accuracy. That is, it is possible to eliminate a quantification error caused by absorbing the intermediate components as in the case of conventionally using an adsorbent, and the measurement accuracy of the gas chromatograph 100 can be highly improved.

Further, since the reagent 60 is filled as a number of granules in the intermediate gas supply pipeline L3, the pressure loss when the intermediate gas passes through the intermediate gas supply pipeline L3 can be kept constant by making the grain sizes of the granules uniform. Thus, for example, even in the case where the reagent 60 is replaced, it is possible to realize accurate measurement without changing the measurement condition of the gas chromatograph 100 every time the replacement is performed.

Note that the present invention is not limited to the above embodiment.

Figure 2:
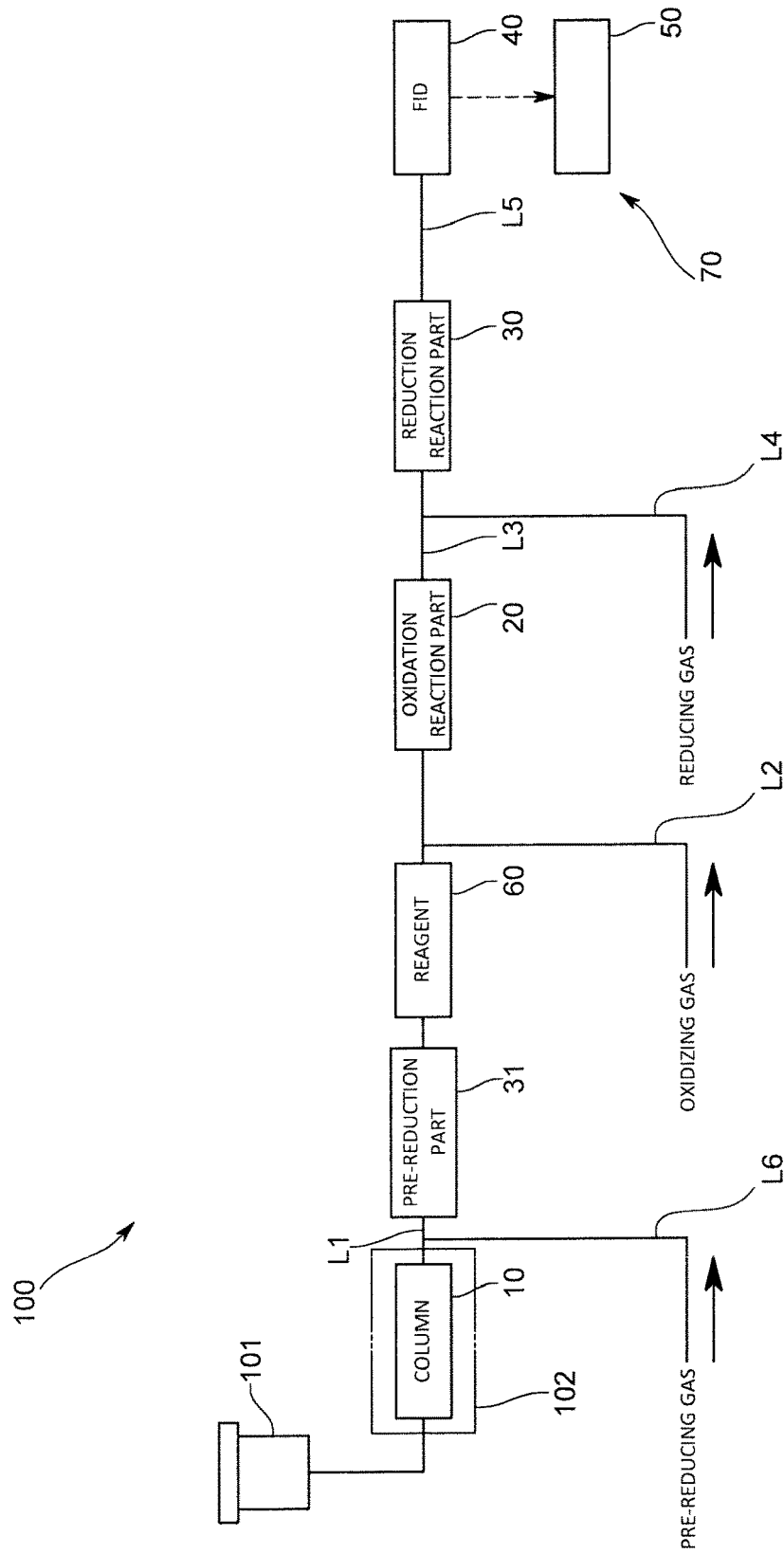
FIG. 2 is a schematic configuration diagram showing an example of a gas chromatograph according to another embodiment.

As shown in FIG. 2, it is possible to provide the reagent 60 upstream side of the oxidation reaction part 20. For example, a pre-reduction part 31 and pre-reduction gas line L6 that introduces pre-reduction gas to the pre-reduction part 31 may be provided between the column 10 and the oxidation reaction part 20. In this case, hydrogen halide is generated based on following chemical reaction shown as following chemical formula before gas is introduced into the oxidation reaction part 20.

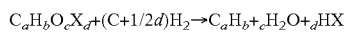

Here X is halogen such as F, Cl, Br, I.

In order to prevent the hydrogen halide HX from being introduced to the oxidation reaction part 20 and from deteriorating oxidation catalyst, the reagent 60 is provided between the pre-reduction part 31 and the oxidation reaction part 20.

According to this embodiment of FIG. 2, both the oxidation reaction part 20 and the reduction reaction part 30 can be protected from halogen X and can obtain the almost same effect of the embodiment of FIG. 1.

Although the metal element contained in the reagent is silver in the above embodiment, it is possible to use other less likely oxidized metals such as platinum. The reagent may contain only a metal element and also may contain further other elements. Moreover, the elements contained in the reagent may be ones so long as the elements react with the measurement non-related components to produce stable compounds in a state of being provided in the intermediate gas flow path. For example, even in the case where a metal element is oxidized and is unreactive with the measurement non-related components when it is not provided in the intermediate gas flow path, such an element may be used so long as a state thereof is changed and exhibits reactivity with the measurement non-related components when provided in the intermediate gas flow path. As a metal element contained in this reagent, there can be exemplified a metal element of which an oxide reacted with only oxygen has a decomposition temperature equal to or lower than 1,000° C. That is, as the reagent, there may be used a compound of a metal element and oxygen bonded with additional elements, but adoptability of the metal element is determined with reference to an oxide of the metal element reacted with only oxygen and based on whether or not the decomposition temperature of the oxide is equal to or lower than 1,000° C. For example, in the case of producing an oxide (copper oxide) by combining copper with only oxygen, the decomposition temperature thereof for decomposing the copper oxide to obtain pure copper is necessarily raised up to a high temperature of 1,800° C. This metal element like copper is excluded from the metal elements for composing the reagent. Note that a lower limit of the decomposition temperature may be equal to or higher than a room temperature. That is, the decomposition temperature of the oxide of the metal element reacted with only oxygen may be 20° C. or higher and 1,000° C. or lower.

Further, as a configuration for providing the reagent in the intermediate gas flow path so as to keep the pressure loss constant, it is not limited to the configuration of carrying the reagent by the porous silica as a support. For example, the reagent of metal and the like components may be supported by spherical glass beads as supports, and the reagent may be supported by fibers such as nonwoven fabric as a support in the intermediate gas supply pipeline. Further, the reagent may be supported in grids of a metal mesh and the like as a support. By providing any of these supports in the intermediate gas supply pipeline, it is possible to sufficiently react the intermediate gas with the reagent and prevent the measurement non-related components from reaching the reduction reaction part while keeping the pressure loss at a predetermined constant value.

As further another embodiment, the reagent may be coated on an inner surface of the intermediate gas supply pipeline.

Although the measurement target components are organic compounds in the above embodiment, other compounds excluding organic compounds such as nitrogen compounds may be used. In addition, the present invention may be configured as a gas chromatograph intermediate processing apparatus that includes:

an oxidation reaction part into which a sample gas passed through a column is introduced and which oxidizes a measurement target component and converts the resultant measurement target component to a prescribed intermediate component to be led out therefrom;

a reduction reaction part into which the intermediate component is introduced and which reduces the intermediate component and converts the resultant intermediate component to a prescribed derivative to be led out therefrom; and an intermediate gas flow path which supplies the intermediate component led out from the oxidation reaction part to the reduction reaction part, and in this configuration, the reagent to be reacted with measurement non-related components is provided in the intermediate gas flow path.

Although the reduction reaction part is provided between the oxidation reaction part and the analysis part in the above embodiment, the present invention may be used for a gas chromatograph or a gas chromatograph intermediate processing apparatus configured so that, without using the reduction reaction part, the concentrations of intermediate components $CO_2$ and CO led out from the oxidation reaction part to the intermediate gas flow path are measured by the analysis part equipped with such as NDIR to thereby perform a qualitative or quantitative determination of the measurement target component. That is, the intermediate gas flow path deriving the intermediate components from the oxidation reaction part is directly connected to the analysis part. In this arrangement, even in the case where the reagent is provided in the intermediate gas flow path, it is possible to prevent occurrence of damage on the pipeline and a quantification error due to the measurement non-related components as in the above embodiment.

In addition, the present invention is not limited to the above embodiments and it is needless to say that various modifications of the embodiments can be made without departing from the spirit of the invention.

DESCRIPTION OF REFERENCE NUMERALS

100 . . . Reaction gas chromatograph
10 . . . Column
20 . . . Oxidation reaction part
30 . . . Reduction reaction part
40 . . . Concentration detecting means
50 . . . Arithmetic device
L3 . . . Intermediate gas supply pipeline (intermediate gas flow path)
60 . . . Reagent

The invention claimed is:
1. A gas chromatograph intermediate processing apparatus comprising:
an oxidation reaction part into which a sample gas passed through a column is introduced and which converts a measurement target component to a prescribed intermediate component to be led out therefrom by oxidation;
an intermediate gas flow path into which the intermediate component led out from the oxidation reaction part is introduced;
a reduction reaction part into which the intermediate component is introduced from the intermediate gas flow path and which converts the resultant intermediate component to a prescribed derivative to be led out therefrom by reduction;

a reagent to be reacted with measurement non-related components is provided in the intermediate gas flow path between the oxidation reaction part and the reduction reaction part or an upstream side of the oxidation reaction part; and a reducing gas pipeline that supplies the reducing gas to the downstream side of the reagent, wherein the reagent contains a metal element, wherein the metal element contained in the reagent is silver, wherein an oxide constituted from only the metal element and oxygen has a decomposition temperature that is equal to or lower than 1,000° C.

2. The gas chromatograph intermediate processing apparatus according to claim 1, wherein the silver reacts with halogen compounds or sulfur compounds that is the measurement non-related components.

3. The gas chromatograph intermediate processing apparatus according to claim 1, wherein the reagent is supported by a support.

4. The gas chromatograph intermediate processing apparatus according to claim 3, wherein the support is a synthetic material.

5. The gas chromatograph intermediate processing apparatus according to claim 1, wherein the reagent is supported by a support formed to be granular and constitutes a granule together with the support, and a plurality of said granules are filled in the intermediate gas flow path.

6. The gas chromatograph intermediate processing apparatus according to claim 1, wherein at least a portion of a pipeline at a portion where the reagent is provided in the intermediate gas flow path is formed to be transparent or translucent.

7. The gas chromatograph intermediate processing apparatus according to claim 1, wherein the oxide constituted from only the metal element and oxygen has a decomposition temperature in a range from 20° C. to 1,000° C.

8. A gas chromatograph intermediate processing apparatus comprising:

an oxidation reaction part into which a sample gas passed through a column is introduced and which converts a measurement target component to a prescribed intermediate component to be led out therefrom by oxidation;

an intermediate gas flow path into which the intermediate component led out from the oxidation reaction part is introduced;

a reduction reaction part into which the intermediate component is introduced from the intermediate gas flow path and which converts the resultant intermediate component to a prescribed derivative to be led out therefrom by reduction;

a reagent to be reacted with measurement non-related components is provided in the intermediate gas flow path between the oxidation reaction part and the reduction reaction part; and a reducing gas pipeline that supplies the reducing gas to the downstream side of the reagent, wherein the reagent contains silver as a metal element.

9. A gas chromatograph comprising:

a column through which a sample gas is passed and which separates various measurement target components contained in the sample gas;

a gas chromatograph intermediate processing apparatus comprising:

an oxidation reaction part into which a sample gas passed through the column is introduced and which converts a measurement target component to a prescribed intermediate component to be led out therefrom by oxidation;

an intermediate gas flow path into which the intermediate component led out from the oxidation reaction part is introduced;

a reduction reaction part into which the intermediate component is introduced from the intermediate gas flow path and which converts the resultant intermediate component to a prescribed derivative to be led out therefrom by reduction;

a reagent to be reacted with measurement non-related components is provided in the intermediate gas flow path between the oxidation reaction part and the reduction reaction part or an upstream side of the oxidation reaction part, wherein the reagent contains a metal element, wherein the metal element contained in the reagent is silver, wherein an oxide constituted from only the metal element and oxygen has a decomposition temperature that is equal to or lower than 1,000° C.; and a reducing gas pipeline that supplies the reducing gas to the downstream side of the reagent; and an analysis part adapted to measure the intermediate component led out from the oxidation reaction part or a derivative led out from the reduction reaction part to analyze the measurement target components.

* * * * *